US006176973B1

(12) United States Patent
Norlander

(10) Patent No.: US 6,176,973 B1
(45) Date of Patent: Jan. 23, 2001

(54) ABSORBENT MATERIAL, ABSORBENT BODY OF THE MATERIAL, AND METHOD FOR PREPARATION OF THE SAME

(75) Inventor: Leif Norlander, Falun (SE)

(73) Assignee: Stora Kopparbergs Bergslags Aktiebolag (PUBL), Falun (SE)

( * ) Notice: Under 35 U.S.C. 154(b), the term of this patent shall be extended for 0 days.

(21) Appl. No.: 08/981,873

(22) PCT Filed: Jun. 25, 1996

(86) PCT No.: PCT/SE96/00831

§ 371 Date: Jan. 5, 1998

§ 102(e) Date: Jan. 5, 1998

(87) PCT Pub. No.: WO97/02844

PCT Pub. Date: Jan. 30, 2000

(30) Foreign Application Priority Data

Jul. 7, 1995 (SE) .................................. 9502486

(51) Int. Cl.[7] ............................ D21H 11/20; D21H 17/06
(52) U.S. Cl. .......................... 162/157.6; 162/9; 162/182; 162/184; 8/116.1; 8/116.4; 8/120; 428/364; 428/375; 428/368; 604/375
(58) Field of Search ................................ 162/157.1, 157.6, 162/9, 182, 184, 158; 8/116.1, 116.4, 120; 604/375, 378; 428/361, 359, 375, 364, 393

(56) References Cited

U.S. PATENT DOCUMENTS

| 2,622,960 | * | 12/1952 | Woods | 8/116.4 |
| 2,785,995 | * | 3/1957 | Kress | 162/158 |
| 4,472,167 | * | 9/1984 | Welch | 8/116.4 |
| 4,853,086 | * | 8/1989 | Graef | 162/157.6 |
| 4,888,093 | * | 12/1989 | Dean et al. | 162/157.6 |
| 5,137,537 | * | 8/1992 | Herron et al. | 8/120 |
| 5,160,789 | * | 11/1992 | Barcus et al. | 428/361 |
| 5,183,707 | * | 2/1993 | Herron et al. | 428/364 |
| 5,549,791 | * | 8/1996 | Herron et al. | 162/157.6 |
| 5,779,857 | * | 7/1998 | Norlander | 162/157.6 |

FOREIGN PATENT DOCUMENTS

WO 95/00703    1/1995  (WO).

* cited by examiner

Primary Examiner—Stanley S. Silverman
Assistant Examiner—Jose A. Fortuna
(74) Attorney, Agent, or Firm—Nixon & Vanderhye

(57) ABSTRACT

An absorbent cellulose product includes cellulose fibers which are cross-linked by reaction with an effective quantity of one or more water-soluble polymers which are produced in advance, which have an average molecular weight of between 350 and 70,000 g/mol, and which possess free acid or aldehyde groups. When the product is being prepared, the cellulose fibers are impregnated with the polymers in aqueous solution. The impregnated substance is dried and defibered at the latest after drying, after which the defibered cellulose fibers are cross-linked in the dry state by means of heating the impregnated, dried and defibered cellulose product.

22 Claims, No Drawings

ABSORBENT MATERIAL, ABSORBENT BODY OF THE MATERIAL, AND METHOD FOR PREPARATION OF THE SAME

TECHNICAL FIELD

The invention relates to an absorbent material, substantially consisting of cellulose, in particular fluff pulp, and to a method for preparing the material, comprising defibering, i.e. individualizing the cellulose fibres and crosslinking them. The invention also relates to an absorbent body in which the material is included as the main component. A method for producing material which is used as a crosslinking agent for cellulose is also dealt with.

1. State of the Art

There has been an interest in chemically crosslinked fluff pulp for many years and it has been proposed that this pulp should be used in absorbent hygiene products. This proposal has first and foremost been based on the satisfactory properties of the crosslinked cellulose, especially with regard to absorption capacity, wet specific volume and absorption rate, properties which are particularly important when producing absorbent hygiene products such as nappies, sanitary towels, etc.

Several authors have proposed using di-, tri- or poly-functional carboxylic acids as the crosslinking reagent and performing the crosslinking reaction in the dry state.

WO 95/00703 (Norlander) describes an absorbent cellulose product which is characterized in that it possesses a fibre structure having improved compressibility under the influence of heat and pressure, which structure can be obtained by crosslinking cellulose fibres, which are impregnated with an effective quantity of crosslinking agent and at least one di-, tri- or poly-functional alcohol, in the dry state, with the fibres being individualized, i.e. defibered, prior to carrying out the crosslinking reaction. Di-, tri- or poly-functional organic acids, and also di-, tri- or poly-functional aldehydes, are mentioned, inter alia, as suitable crosslinking substances. The compressibility of the defibered and crosslinked cellulose product is influenced by adding a di-, tri- or poly-functional alcohol, expediently together with the crosslinking reagent. A suggested hypothesis regarding a probable chemical mechanism involves the hydroxyl groups of the polyfunctional alcohols reacting with the crosslinking reagent in the same manner as the hydroxyl groups of the cellulose. In this way, the alcohols are bound by covalent bonds to the cellulose molecule, whose swelling state is altered, with the resilience decreasing in the dry state. The cellulose fibres which are chemically crosslinked in this manner can be compressed to a substantially higher density, at greatly reduced pressure, as compared with cellulose fibre which is crosslinked in the dry state without any of the said alcohols being added. According to the said WO 95/00703, the cellulose fibres are crosslinked at a temperature which is expediently between 140 and 210° C. Despite the fact that it is suggested that alcohols having boiling points which exceed the temperature of the crosslinking reaction should be used in combination with the crosslinking reagent, it has nevertheless been found that there is a substantial emission of polyol (di-, tri- or poly-functional alcohol) in exhaust air from the reaction chamber for the crosslinking reaction. This implies environmental pollution with organic compounds and/or demands the installation and maintenance of purification equipment for the exhaust air from the plant. In addition, the emission involves a substantial loss of active compound.

2. Brief Disclosure of the Invention

The object of the present invention, like that of the invention which is described in WO 95/00703, is to offer a fibred cellulose product which is of the type specified in the preamble, which possesses a fibre structure having, as compared with the prior art, an improved, preferably controllable, compressibility, and which can be used in absorbent products, especially in absorption bodies which are intended to collect body fluids, for example those products which include baby nappies, sanitary towels and incontinence products, and especially to be able to offer thinner and more comfortable absorbent products—but nevertheless possessing good absorption properties—but with a substantially reduced emission of organic compounds when carrying out the crosslinking reaction (the setting).

These and other objects can be achieved by crosslinking the cellulose fibre by means of reacting the cellulose with an effective quantity of one or more water-soluble polymers, which have been prepared in advance, which have an average molecular weight, Mw, of between 350 and 70,000 g/mol, preferably between 350 and 25,000 g/mol, and expediently between 450 and 10,000 g/mol, and which possess free acid or aldehyde groups. Good results have been achieved using water-soluble polymers which have been produced by means of reacting at least one first di-, tri- or poly-functional compound, which is not a polyol, with at least one polyol, so that the said polymers are obtained which possess free acid or aldehyde groups. Typically, in these cases, the crosslinking substance consists of a mixture of water-soluble polymers which comprises reaction products of the type FP, $FP_2$, $F_2P$, $F_2P_2$, $F_2P_3$, etc., where F is that part of the polymer molecule which derives from the said first compound and P is that part of the polymer molecule which derives from the said polyol (di-, tri- or poly-functional alcohol). The polymers/oligomers possess functional groups, such as carboxyl or aldehyde, which are able to react with the hydroxyl groups of the cellulose on heating and, where appropriate, in the presence of a catalyst. If, for example, citric acid is reacted with glycerol, a series of polymers, especially oligomers, is formed: FP, $FP_2$, $F_2P_2$, etc., where FP has a molecular weight Mw=266 g/mol. By means of using this product, which has been prepared in advance, as the crosslinking agent, the emission of glycerol from the crosslinking reaction oven can be reduced to less than 10% of the emission which has been measured when citric acid and glycerol are added separately, in accordance with the said WO 95/00703, and only brought to react with the cellulose fibres, and with each other, in connection with carrying out the crosslinking reaction.

In order further to reduce the emission of polyol, and also in order to offer a cellulose product which is improved still further, a di-, tri- or poly-functional alcohol having a higher molecular weight than glycerol, for example trimethylolpropane (TMP), can be used as the polyol. By means of polymerizing the citric acid and TMP using an esterification reaction, the quantity of free TMP in the fibre is reduced when the crosslinking reaction is carried out, which is analogous to the results obtained from the system citric acid and glycerol and which results in the emission of TMP in exhaust air from the crosslinking plant decreasing to an even greater extent than in the case of the system citric acid and glycerol.

The invention can be said to be a result of efforts to offer an absorbent cellulose product which, from the point of view of the user, possesses properties which are essentially at least as good as those of the product which is described in the said WO 95/00703 at the same time as the undesirable emission of chemicals during the setting reaction is essentially eliminated. These aims can be achieved by, for example, those chemicals which are added to the pulp separately, or at least unreacted, in accordance with WO 95/00703, being reacted with each other in advance so that a water-soluble polymer mixture is obtained which possesses functional acid or aldehyde groups. Experiments have demonstrated that the cellulose can be crosslinked with this polymer which has been prepared in advance, with the crosslinked pulp having the same satisfactory properties as were obtained when the preparations were added separately to the pulp. These results are surprising on the basis of the theories propounded in WO 95/00703. Without binding the invention to any novel or special theory, it is the inventor's judgement that that which is important for achieving the desired results is that water-soluble compounds, which on the one hand possess acid groups or aldehyde groups which are functional for the crosslinking and on the other exhibit a certain minimum molecular weight, are used as the crosslinking reagent, while it may be of less importance which particular compound is the carrier of the functional groups.

On the basis of this theory, it should not only be the said copolymers of the FP, $FP_2$, $F_2P$, $F_2P_2$, etc. type which can be used as crosslinking agents, but also other copolymers or polymers which are produced by polymerizing functional monomers, for example polymerized acids, having, for example, functional carboxyl groups, or polymerized monofunctional aldehydes. This can also be expressed in the same way as has been done above, namely that one or more water-soluble polymers, preferably oligomers, which have been produced in advance, which exhibit an average molecular weight of between 350 and 70,000 g/mol, preferably between 350 and 25,000 g/mol, and expediently between 450 and 10,000 g/mol, and which possess free acid or aldehyde groups, are used as the crosslinking agent for the cellulose.

Average molecular weight, Mw, is defined in accordance with the following equation (Fred W. Billmeyer, JR, Textbook of Polymer Science, sec. ed. p. 78):

$M_w = \Sigma w_i M_i$, in which $M_w$=weight-average molecular weight $w_i$=weight fraction $M_i$=molecular weight of weight fraction The said first compound which is caused to react with the said polyol for the purpose of producing a crosslinking chemical can consist of a compound which contains functional groups of the group types which include di-, tri- or poly-functional carboxyl groups or aldehyde groups, or acid anhydride groups.

Compounds which can be used as the said first compounds, and which contain di-, tri- or poly-functional carboxyl groups (COOH), can be sought from among the carboxylic acids which include, for example, citric acid, 1,2,3-tricarboxypropionic acid, 1,2,3,4-tetracarboxybutyric acid, etc.

Compounds which can be used as the said first compounds, and which contain di-, tri- or poly-functional aldehyde groups (COH), can be sought from among the aldehydes which include, for example, glyoxal, glutaraldehyde, etc.

Compounds which can be used as the said first compounds, and which contain acid anhydride groups, can be sought from among the acid anhydrides which, for example, include maleic anhydride and phthalic anhydride.

A di-, tri- or poly-functional alcohol having a molecular weight which exceeds 60 g/mol is expediently used as the polyol in the preliminary production of the crosslinking reagent. The carbon skeleton of the said alcohols can, where appropriate, also contain heteroatoms, for example oxygen or nitrogen. In addition, the polyfunctional alcohols can, where appropriate, contain one or two polar functional groups of the aldehyde group or carboxyl group type.

The method according to the invention thus involves the cellulose fibres being impregnated with a quantity, which is effective for crosslinking, of one or more water-soluble polymers which are produced in advance, which have an average molecular weight, Mw, of between 350 and 70,000 g/mol, preferably of between 350 and 25,000 g/mol, and expediently of between 450 and 10,000 g/mol, and which possess free acid or aldehyde groups, after which the impregnated substance is dried. At the very latest after drying, the cellulose is defibered, after which the defibered cellulose fibres are crosslinked in the dry state by means of heating the impregnated, dried and defibered cellulose product at a temperature of between 100 and 210° C., preferably at a temperature of between 120° C. and 210° C., expediently of between 140 and 200° C.

Superabsorbent polymer (SAP), in powder or fibre form, can also be incorporated into the absorbent cellulose product. In this context, SAP is defined as polymers which can form gels containing at least 10 g of water per g of polymer. Certain applications can require the pulp to be reinforced using long fibres, which increase the tear strength. While viscose fibres and polyester fibres are examples of fibres which have this effect, other polymeric fibres can also be used. In this way, webs can be formed which are sufficiently strong to be included in processes in which webs of special density can be cut to size and placed at the desired site in absorbent products. Increased strength is also desirable for products having low grammages, in order to ensure that the absorption body does not rupture in the final product.

For optimal use of the cellulose fibre, products according to the invention having density gradients should probably be produced, for example, by webs being formed and pressed to different densities before being laid together, or by pulp having different compressibilities, achieved, for example, by varying the crosslinking and/or other chemicals with which the cellulose fibres are impregnated, being formed into air-laid or wet-laid webs and then pressed in a common press nip. An absorption body having a density gradient can be formed in this way. The number of layers which are used in the absorbent product, and the densities of the different layers, can be determined by the intended area of application. For products which are to be loaded with large quantities of liquid over a short time period, it can be expedient to have an upper layer of low density, which upper layer can face the wearer of the absorption product, while the layer(s) which is/are connected to it can be compressed to (a) higher density(ies).

Nowadays, a baby nappy of modern type is packed at an average density of 130–170 kg/m³. The pulp according to the invention affords excellent possibilities for increasing the average density of the absorption body in absorbent products and thereby lowering the costs of transporting and storing these products.

The pulp according to the present invention can also be formed into fibre webs of high density. The fibre webs can be formed either using a dry or a wet forming technique, with the fibre being dispersed in air or water in conjunction with the web being formed on a wire. These webs can be reeled into reels of high density, which can considerably reduce the cost of transporting and storing the pulp as a semi-finished product. After that, the fibre web can be fibred, for example in a hammer mill, and then formed into products of the desired density, which density can be markedly lower than the original density of the pulp and depend entirely on the demands which are placed on the absorption properties of the final product. Alternatively, the web can be cut into pieces of the desired size and placed directly in the desired position in the absorbent product. A very great advantage in this connection is that pulp containing the cellulose fibres according to the invention which are crosslinked in the dry can be used in that type of equipment which is nowadays available for producing nappies (also for producing incontinence pads) and in machines for manufacturing sanitary towels and air-formed paper.

Furthermore, such reinforcement fibres can be of interest when manufacturing pulp webs which are intended to be fibred in conventional fibering equipment, for example in a hammer mill, for use at a lower density than the density of the original pulp web. The reinforcement fibres then contribute to creating a fibre structure having low density and good absorption properties and also substantially increased strength.

Expediently, the cellulose fibres are impregnated with 5–100 g/kg of the crosslinking reaction product which is prepared in advance and which essentially consists of a mixture of polymers which are water-soluble. The following procedure can be employed when producing the compressible fluff pulp which is crosslinked in the dry. The cellulose fibres are impregnated with an aqueous solution containing the crosslinking polymer mixture. The quantity of crosslinking reaction product which is added to the cellulose fibre is adjusted within the range of 5–100 g of reaction product per kg of cellulose fibre. Preferably, the quantity of crosslinking reaction product is adjusted to the range of 20–60 g per kg of cellulose fibre.

The cellulose fibre is then formed into a web, which is dried at temperatures which are low enough to ensure that the crosslinking reagent is not activated prior to the subsequent fibre exposure, which then takes place in the dry state, i.e. at a dry matter content which exceeds 80%, and is preferably between 90 and 95%. The dry fibering is expediently carried out using a hammer mill. Alternatively, the cellulose fibre is fibered prior to the drying process, in the wet state, which results in the cellulose fibre spiralling during drying, which is well known from the manufacture of so-called flash-dried pulp. Fibering in the wet state is carried out at a dry matter content of 30–80%, preferably at 40–55%.

The exposed/individualized and dried cellulose fibre is crosslinked in the dry and exposed state by means of the crosslinking agent which has been supplied being activated by being heated to reaction temperature. Preferably, the material is heated by the exposed cellulose fibre being dispersed in warm air. The reaction temperatures which are required depend on the crosslinking reagent which is used. In order to achieve industrially acceptable reaction times, the reaction is performed at a temperature between 100° C. and 210° C., preferably at a temperature between 120° C. and 210° C., expediently between 140° C. and 200° C. The crosslinking reaction is carried out with a dwell time of between 1 and 20 minutes, preferably of between 4 and 10 minutes.

The crosslinking can be catalyzed by so-called Lewis acids, for example iron(III) chloride, zinc(II) chloride or magnesium(II) chloride. Substances selected from the alkali metal hypophosphite, alkali metal polyphosphate, alkali metal phosphate and alkali metal sulphate groups, sodium fluoroborate, disodium carbonate, and organic amines, can also catalyze the crosslinking reaction. The choice of catalyst is determined by the functional groups possessed by the polymeric crosslinking reagent.

Cellulose fibres for crosslinking according to the invention can be selected from the bleached, partially bleached and unbleached, sulphate- or sulphite-delignified, softwood or hardwood fibre groups. The cellulose fibre can furthermore be selected from the thermomechanical and chemothermomechanical pulp groups. In principle, pulps obtained from grass-like, etc., raw materials can also be used.

Additional features and aspects, and also advantages, of the invention are evident from the attached patent claims and from the following account of undertaken experiments and from the subsequent description of a preferred embodiment of the method according to the invention.

DESCRIPTION OF EXPERIMENTS WHICH WERE UNDERTAKEN

Crosslinking Agent and its Preparation

When the polymeric crosslinking agent is being prepared, the two reagents are weighed and added to a reaction vessel. In experiments which were carried out in the laboratory, the material was heated on a thermostatted oil bath and maintained at the reaction temperature while being stirred.

Experiment 1

50 mol % each of citric acid and glycerol were added to a beaker and heated at 138–148° C. (approx. 140° C.) for 3 h. The structural formulae of the starting compounds, and proposals for probable reaction products, are given below, where F = citric acid
P = glycerol
nCOOH = number of functional carboxyl groups
Mw = molecular weight

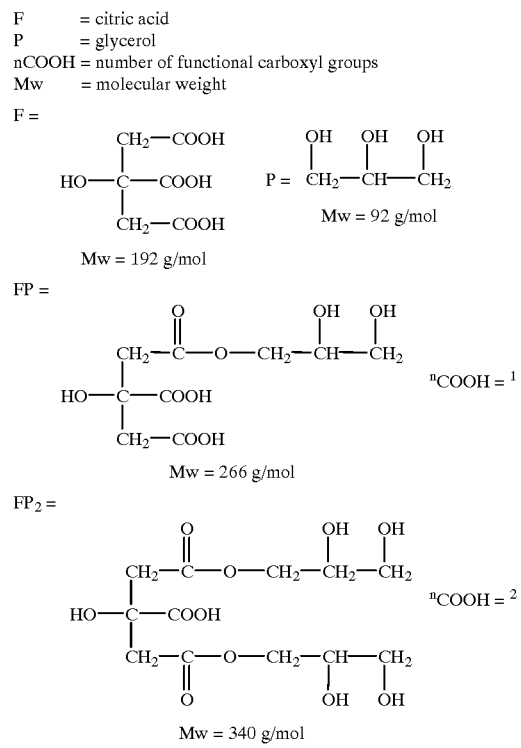

-continued

F₂P = 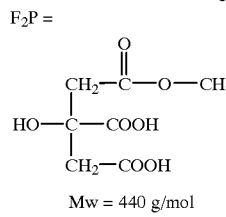

Mw = 440 g/mol     nCOOH = 4

F₂P₂ = 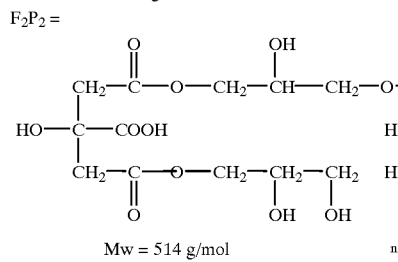

Mw = 514 g/mol     nCOOH = 3

The reaction products were analysed by gel permeation chromatography (GPC). Content data and the molecular weights of probable reaction products were recorded from chromatograms. The average molecular weight, Mw, was also calculated in accordance with the above definition. The gel permeation chromatograph was equipped with 2 Ultrastyragel 500 Å columns and 1 Ultrastyragel 100 Å column. The column system was calibrated with respect to molecular weight using a polyethene oxide standard having a narrow molecular weight distribution, Mw=800, 1,200 and 2,000 g/mol, and various acids and alcohols in the molecular weight range of 92–276 g/mol. THF (tetrahydrofuran) was used as the eluent, with a flow rate of 1 ml/min. The reaction products were dissolved in THF and 100 μl of a 1% solution were injected manually. A refractive index detector was used as the detector. Content data are based on the assumption that the response factor is the same for all the components. However, this assumption is not entirely correct since, for example, citric acid gives a stronger response than does glycerol, with the ratio being 1.28:1. Consequently, the content data for reaction products and starting material are not entirely exact, but this situation is unlikely to affect the conclusions which are presented below. The content data, in accordance with the above, the molecular weights of certain probable reaction products, the molecular weight according to GPC, the maximum molecular weight according to GPC, and the calculated weight-average molecular weight according to the definition on page 5, obtained in various experiments are recorded below.

Table 1 records the proportions of a selection of probable reaction products from the esterification reactions between citric acid and glycerol.

TABLE 1

Citric acid/glycerol, 50/50 mol %, 3 h
Temp.: 140° C.

| Retention time min | Area-conc. | Mw (GPC) g/mol | Probable product | Mw- Probable product g/mol | nCOOH |
|---|---|---|---|---|---|
| 21.11 | 0.1195 | 803 | | | |
| 21.81 | 0.3346 | 620 | F2P | 440 | 4 |
| 22.93 | 0.084 | 409 | FP2 | 340 | 1 |
| 23.48 | 0.21 | 333 | FP | 266 | 2 |
| 24.21 | 0.1367 | 254 | F | 192 | 3 |

TABLE 1-continued

Citric acid/glycerol, 50/50 mol %, 3 h
Temp.: 140° C.

| Retention time min | Area-conc. | Mw (GPC) g/mol | Probable product | Mw- Probable product g/mol | nCOOH |
|---|---|---|---|---|---|
| 26.47 | 0.0466 | 110 | P | 92 | |
| Total | 0.9314 | | Weight- average Mw mol 480: | | |

Highest Mw = 1000 g/mol

Experiment 2

Citric acid and glycerol were added in the same molar ratio as in Experiment 1. The mixture was then reacted for 3 h at approx. 150° C., i.e. at a somewhat higher temperature than in Experiment 1. The results are presented in Table 2.

TABLE 2

Citric acid/glycerol, 50/50 mol %, 3 h
Temp.: 150° C.

| Retention time min | Area-conc. | Mw (GPC) g/mol | Probable product | Mw- Probable product g/mol | nCOOH |
|---|---|---|---|---|---|
| 20.33 | 0.256 | 1073 | | | |
| 20.97 | 0.1851 | 846 | | | |
| 21.89 | 0.2375 | 601 | F2P | 440 | 4 |
| 23.05 | 0.0536 | 391 | FP2 | 340 | 1 |
| 23.59 | 0.1367 | 320 | FP | 266 | 2 |
| 24.34 | 0.0938 | 242 | F | 192 | 3 |
| 26.62 | 0.0236 | 104 | P | 92 | |
| Total | 0.9863 | Weight- average Mw g/mol 673 | | | |

Highest Mw = 1400 g/mol

Experiment 3

49 mol % of citric acid, 49 mol % of glycerol and, as catalyst, 2 mol % of $H_3PO_4$ were mixed and reacted at 150° C. for 2 h. The results are presented in Table 3.

TABLE 3

Citric acid/glycerol/$Na_2HPO_4$, 49/49/2 mol %
Temp.: 150° C.

| Retention time min | Area-conc. | Mw (GPC) g/mol | Probable product | Mw- Probable product g/mol | nCOOH |
|---|---|---|---|---|---|
| 20.5 | 0.1 | 1008 | | | |
| 20.98 | 0.205 | 843 | | | |
| 21.9 | 0.275 | 599 | F2P | 440 | 4 |
| 23.05 | 0.0662 | 391 | FP2 | 340 | 1 |
| 23.6 | 0.1698 | 319 | FP | 266 | 2 |
| 24.34 | 0.118 | 242 | F | 192 | 3 |
| 26.6 | 0.0346 | 105 | P | 92 | |
| Total | 0.9686 | Weight- average Mw g/mol 558 | | | |

Highest Mw = 1200 g/mol

Experiment 4

In this case, the first compound consisted of maleic anhydride, $C_4H_2O_3$, which has the structural formula:

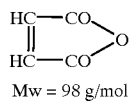

$Mw = 98$ g/mol

Maleic anhydride and glycerol were added in a mol % ratio of 70/30 and the mixture was reacted at 94–97° C. for 3 h. The reaction product was analyzed by gel permeation chromatography and it was observed that the quantity of unreacted maleic anhydride+glycerol was approx. 11%, while the remainder consisted of a mixture of polymers of the FP, $FP_2$, $F_2P$, $F_2P_2$, etc., type. These polymers have the following structural formulae and molecular weights, with F being derived from maleic anhydride and P from glycerol.

FP

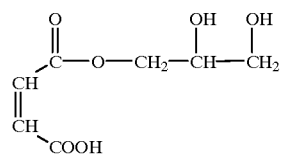

$Mw = 190$ g/mol $F_2P$

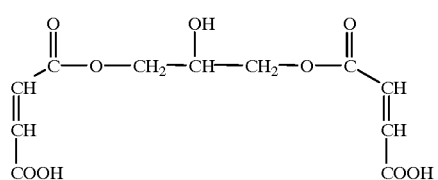

$Mw = 288$ g/mol $F_3P$

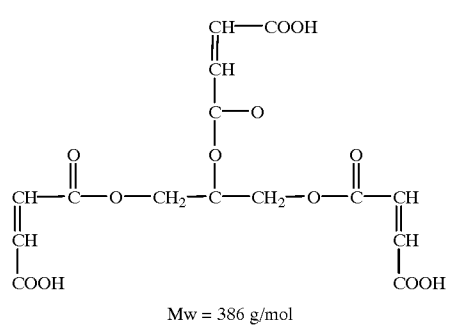

$Mw = 386$ g/mol

The proportions of the different polymeric/oligomeric reaction products, the number of carboxylic acid groups in the abovementioned products, and the molecular weight, are given in Table 4.

TABLE 4

Maleic anhydride/glycerol, 70/30 mol %, 3 h
Temp.: 100° C.

| Retention time min | Area-conc. | Mw (GPC) g/mol | Probable product | Mw-Probable product g/mol | nCOOH |
|---|---|---|---|---|---|
| 20.5 | 0.047 | 1008 | | | |
| 21.79 | 0.1 | 624 | | | |

TABLE 4-continued

Maleic anhydride/glycerol, 70/30 mol %, 3 h
Temp.: 100° C.

| Retention time min | Area-conc. | Mw (GPC) g/mol | Probable product | Mw-Probable product g/mol | nCOOH |
|---|---|---|---|---|---|
| 22.22 | 0.1 | 532 | | | |
| 22.87 | 0.094 | 418 | $F_3P_2$ | 460 | 2 |
| 23.54 | 0.41 | 326 | $F_3P$ | 386 | 3 |
| 24.66 | 0.0981 | 215 | $F_2P$ | 288 | 2 |
| 25.25 | 0.0199 | 173 | FP | 190 | 1 |
| 25.65 | 0.0206 | 149 | F | 98 | |
| 26.02 | 0.0913 | 130 | P | 92 | |
| Total | 0.9809 | Weight-average Mw g/mol 380 | | | |

Highest Mw = 1200 g/mol

Experiment 5

Citric acid and trimethylolpropane (TMP) were added in the molar ratio of 55/45 mol % and reacted at approx. 140° C. (137–142°) for 3 h. The structural formulae of the starting compounds and the results are presented below and in Table 5, where F     = citric acid
P     = trimethylolpropane (TMP)
nCOOH = number of functional caroboxyl groupd
Mw    = molecular weight F =
Citric acid $$\begin{array}{c} CH_2-COOH \\ | \\ HO-C-COOH \\ | \\ CH_2-COOH \end{array}$$

$Mw = 192$ g/mol

P =
TMP $$CH_3-CH_2-\underset{\underset{CH_2OH}{|}}{\overset{\overset{CH_2OH}{|}}{C}}-CH_2OH$$

$Mw = 134$ g/mol

FP =

$$CH_3-CH_2\underset{\underset{CH_2}{|}}{C}-CH_2OH$$
$$\begin{array}{c} | \\ CH_2 \\ | \\ O \\ | \\ C=O \\ | \\ CH_2 \\ | \\ HO-C-COOH \\ | \\ CH_2-COOH \end{array}$$

nCOOH = 2

$Mw = 308$ g/mol

The reaction was taken too far, resulting in a water-swellable, but water-insoluble, polymer. The part which was soluble in THF (tetrahydrofuran) had the molecular weight distribution given in Table 5 below.

TABLE 5

Citric acid/TMP, 55/45 mol %, 3 h
Temp.: 137–142° C.

| Retention time min | Area-conc. | Mw (GPC) g/mol | Probable product | Mw-Probable product g/mol | nCOOH |
|---|---|---|---|---|---|
| 18.02 | 0.49377 | 2531 | | | |
| 20.39 | 0.10234 | 1050 | | | |
| 21.31 | 0.05802 | 746 | | | |
| 21.73 | 0.05972 | 638 | F2P2 | 598 | 3 |
| 22.26 | 0.2378 | 524 | F2P | 482 | 4 |
| 23.03 | 0.07564 | 394 | FP | 308 | 2 |
| 24 | 0.06311 | 275 | F | 192 | 3 |
| 25.63 | 0.1484 | 150 | P | 134 | |
| Total | 0.89122 | Weight-average Mw g/mol 1521 | | | |

Highest Mw = 3400 g/mol

Experiment 6
(Citric acid/TMP, molar ratio 65/35)

TABLE 6

Citric acid/TMP 65/35 mol %, 3 h
Temp.: 137–142° C.

| Retention time min | Area-conc. | Mw (GPC) g/mol | Probable product | Mw-Probable product g/mol | nCOOH |
|---|---|---|---|---|---|
| 17.96 | 0.2938 | 2589 | | | |
| 19.46 | 0.0803 | 1483 | | | |
| 20.01 | 0.0639 | 1209 | | | |
| 20.57 | 0.102 | 982 | | | |
| 21.68 | 0.0927 | 650 | F2P | 598 | 3 |
| 22.97 | 0.042 | 403 | FP | 308 | 2 |
| 23.93 | 0.127 | 282 | F | 192 | 3 |
| 25.55 | 0.00296 | 154 | P | 134 | |
| Total | 0.80466 | Weight-average Mw g/mol 1187 | | | |

Highest Mw = 3400 g/mol

Experiment 7
(Citric acid/TMP, molar ratio 55/45)

TABLE 7

Citric acid/TMP, 55/45 mol %, 1.5 h
Temp.: 137–142° C.

| Retention time min | Area-conc. | Mw (GPC) g/mol | Probable product | Mw-Probable product g/mol | nCOOH |
|---|---|---|---|---|---|
| 20 | 0.1 | 1213 | | | |
| 20.54 | 0.209 | 993 | | | |
| 21.4 | 0.124 | 721 | | | |
| 21.81 | 0.109 | 620 | F2P2 | 598 | 3 |
| 22.38 | 0.0679 | 501 | F2P | 482 | 4 |
| 23.12 | 0.194 | 381 | FP | 308 | 2 |
| 24.12 | 0.142 | 263 | F | 192 | 3 |
| 25.75 | 0.0444 | 143 | P | 134 | |
| Total | 0.9903 | Weight average Mw g/mol | | | |

TABLE 7-continued

Citric acid/TMP, 55/45 mol %, 1.5 h
Temp.: 137–142° C.

| Retention time min | Area-conc. | Mw (GPC) g/mol | Probable product | Mw-Probable product g/mol | nCOOH |
|---|---|---|---|---|---|
| | | 646 | | | |

Highest Mw = 1800 g/mol

Experiment 8
(Citric acid/TMP, molar ratio 65/35)

TABLE 8

Citric acid/TMP 65/35 mol %, 1.5 h
Temp.: 137–142° C.

| Retention time min | Area-conc. | Mw (GPC) g/mol | Probable product | Mw-Probable product g/mol | nCOOH |
|---|---|---|---|---|---|
| 19 | 0.1 | 1759 | | | |
| 20.09 | 0.16 | 1173 | | | |
| 20.71 | 0.138 | 932 | | | |
| 21.39 | 0.0664 | 724 | | | |
| 21.83 | 0.178 | 615 | F2P2 | 598 | 3 |
| 23.13 | 0.117 | 379 | FP | 308 | 2 |
| 24.11 | 0.219 | 264 | F | 192 | 3 |
| 25.76 | 0.12 | 143 | P | 134 | |
| Total | 1.0984 | Weight-average Mw g/mol 780 | | | |

Highest Mw = 1900 g/mol

Preparation of the Cellulose Product—Triggering the Crosslinking Reaction—Product Properties In the series of experiments to be described below, a long-fibered, bleached sulphate fluff pulp (STORA Fluff EC 0.1), which was produced from raw wood material consisting substantially of Scandinavian pine and spruce, was used as the cellulose fibre. A4 sheets of this fluff pulp were conditioned at 23° C., 50% RH (relative humidity) and weighed. The sheets were impregnated by dipping them in aqueous solutions containing dissolved crosslinking chemicals in appropriate concentrations. The excess of liquid was pressed out between blotting paper in a press at a pressure of 5.5 bar. After pressing, the dry matter content was approx. 50%. The sheets were dried on a cylinder drier at 85° C. The uptake of chemicals was determined by weighing. The sheets were then conditioned and defibered in a Kamas HO1 hammer mill at 3500 rpm, so that the fibres were exposed/individualized. The defibered material was heated to setting reaction temperature, i.e. in order to trigger the crosslinking, in a laboratory oven, in which hot air was blown through a bed of the material at about 700 l/min. Unless otherwise indicated, the material as heated to 180° C. and maintained at this crosslinking reaction temperature for 6 min.

Test specimens were prepared by standard methods, and the following material properties were investigated:

grammage
thickness
density
specific volume, dry and wet
absorption and density after pressing absorption capacity/absorption rate These properties were determined using standardized methods which were described in WO 95/00703.

Experimental Series I

The Citric Acid and Glycerol System

The reaction product, in the form of a water-soluble polymer, which was obtained in Experiment 1 by reacting citric acid and glycerol, termed CG polymer here, was used in these experiments as the crosslinking agent according to the invention. The reference material consisted of fluff pulp of the same type which had been crosslinked with citric acid in the presence of glycerol in accordance with the principles described in WO 95/00703. In both cases, 10 g of disodium hydrogen phosphate, $Na_2HPO_4$, were used as catalyst for the crosslinking reaction per kg of pulp.

140 g/cm$^2$ superabsorbent (SAP) were also added to the product when evaluating test samples having the dimensions 12×30 cm. The superabsorbent which is known under the trade name of FAVOR SXM75 (Stockhausen) was used as the superabsorbent. The results are presented in Table 9.

TABLE 9

| Crosslinking agent, g/kg | Citric acid, 35 Glycerol, 25 | CG polymer, 50 | Citric acid, 35 Glycerol 25 | CG polymer 50 |
|---|---|---|---|---|
| Absorption, SCAN: | | | | |
| Dry specific volume, dm$^3$/kg | 20.2 | 20.6 | | |
| Wet specific volume, dm$^3$/kg | 9.9 | 9.8 | | |
| Absorption capacity, g/g | 11.7 | 11.5 | | |
| Absorption after press: | | | | |
| Sheet pressure at 90° C. | 48 | 48 | | |
| Density, kg/m$^3$ | 270 | 274 | | |
| Absorption capacity, g/g | 7.7 | 7.6 | | |
| Wet specific volume, dm$^3$/kg | 8.2 | 8. 1 | | |
| Test samples, 12*30 cm: | | | | |
| Grammage (inc. SAP), g/m$^2$ | 1130 | 1157 | 120.8 | 1123 |
| Thickness (inc. SAP), mm | 4.8 | 4.3 | 3.3 | 3.1 |
| Density (inc. SAP), kg/m$^3$ | 235 | 266 | 370 | 358 |
| Absorption rate: 4 × 50 ml | | | | |
| Dosage 1 ml/s | 2.2 | 2.3 | 1.5 | 1.4 |
| Dosage 2 ml/s | 1.4 | 1.8 | 1.2 | 1.0 |
| Dosage 3 ml/s | 1.0 | 1.3 | 0.84 | 0.77 |
| Dosage 4 ml/s | 0.79 | 0.94 | 0.57 | 0.55 |

Experimental Series II

The Maleic Anhydride and Glycerol System

In Experimental Series II, the following were used as crosslinking agents according to the invention: (a) the reaction product substantially consisting of water-soluble polymer, here termed MG polymer 70/30—3 h, which was obtained in Experiment 4 by reacting maleic anhydride and glycerol, in a molar ratio of 70/30, for 3 h, and (b) reaction products which are obtained by prepolymerizing:

70 mol % of maleic anhydride+30 mol % of glycerol, reaction time 1 h, termed MG polymer 70/30—1 h, 90 mol % of maleic anhydride+10 mol % glycerol, reaction time 1 h, termed MG polymer 90/10—1 h, and 90 mol % of maleic anhydride+10 mol % of glycerol, reaction time 3 h, termed MG polymer 90/10—3 h.

In all cases, the reaction temperature during the polymerization was 94–97° C.

The crosslinking agents were added at the rate of 50 g/kg of pulp. The addition of the crosslinking agents, the treatment of the pulp and the implementation of the crosslinking reaction were described above. In this case too, $Na_2HPO_4$, which was added at the rate of 10 g per kg of pulp, was used as the catalyst during the crosslinking.

The results which were obtained are presented in Table 10.

TABLE 10

| Crosslinking agent, MG polymer: | 70/30 - 1h | 70/30 - 3h | 90/10 - 1h | 90/10 - 3h |
|---|---|---|---|---|
| Absorption, SCAN | | | | |
| Dry specific volume, dm$^3$/kg | 20.7 | 20.9 | 21.6 | 21.8 |
| Wet specific volume, dm$^3$/kg | 9.8 | 9.8 | 10.1 | 10.2 |
| Absorption capacity, g/g | 11.2 | 11.5 | 11.9 | 12.1 |
| Absorption after press: | | | | |
| Sheet pressure at 90° C., bar | 24 | 24 | 23 | 24 |
| Density, kg/m$^3$ | 340 | 339 | 236 | 267 |
| Absorption capacity, g/g | 6.9 | 7.0 | 7.6 | 7.4 |
| Wet specific volume, dm$^3$/kg | 7.6 | 7.5 | 8.4 | 8.1 |
| Sheet pressure at 90° C., bar | 48 | 48 | 47 | 47 |
| Density, kg/m$^3$ | 366 | 360 | 281 | 272 |
| Absorption capacity, g/g | 6.9 | 7.0 | 7.2 | 7.5 |
| Wet specific volume, dm$^3$/kg | 7.5 | 7.6 | 7.9 | 8.2 |

Experimental Series III

The Citric Acid and Trimethylolpropane (TMP) System

The following polymeric/oligomeric reaction products were prepared for use as crosslinking agents:

Polymer A=reaction product from 55/45 mol % citric acid/TMP, 137–142° C., 3 h

Polymer B=reaction product from 65/35 mol % citric acid/TMP, 137–142° C., 3 h

Polymer C=reaction product from 55/45 mol % citric acid/TMP, 137–142° C., 1.5 h

Polymer D=reaction product from 65/35 mol % citric acid/TMP, 137–142° C., 1.5 h

While polymer A swelled, it was not fully soluble in water; on the other hand, B, C and D were.

As regards implementation of the setting reaction, reference is made to the previous description. $Na_2HPO_4$ was used as the catalyst. Fluff pulp which had been crosslinked with citric acid in the presence of TMP was used as the comparison material. SAP, in a quantity of 140 g/m$^2$, target value, was also added to samples of 12×30 cm in size. The results are presented in Table 11.

TABLE 11

| Crosslinking agent, g/kg | Citric acid 38 TMP 22 | Polymer B)60 | Polymer C)60 | Polymer D)60 |
|---|---|---|---|---|
| Uptake chemicals, % | 7.1 | 5.2 | 6.6 | 6.2 |
| Fibering energy, 3500 rpm, kJ/kg | 133 | 145 | 140 | 140 |
| Absorption, SCAN: | | | | |
| Bulk, dm$^3$/kg | 21.8 | 21.8 | 21.9 | 21.5 |
| Wet specific volume, dm$^3$/kg | 10.1 | 9.7 | 9.7 | 10.0 |
| Absorption capacity, g/g | 11.6 | 11.0 | 11.3 | 11.8 |
| Absorption after press: | | | | |
| Sheet pressure at 90° C., bar | 50 | 50 | 50 | 49 |
| Density, kg/m$^3$ | 239 | 311 | 325 | 230 |
| Bulk, dm$^3$/kg | 4.2 | 3.2 | 3.9 | 4.3 |
| Wet specific volume, m$^3$/kg | 7.8 | 7.5 | 7.8 | 8.0 |
| Absorption capacity, g/g | 7.3 | 7.1 | 7.2 | 7.5 |

TABLE 11-continued

| Crosslinking agent, g/kg | Citric acid 38 TMP 22 | Polymer B)60 | Polymer C)60 | Polymer D)60 |
|---|---|---|---|---|
| 12 × 30 cm samples | | | | |
| Grammage (including SAP), g/m² | 1070 | 1120 | 1110 | 1070 |
| Thickness, mm | 3.1 | 3.1 | 3.1 | 3.2 |
| Density, kg/m³ | 340 | 362 | 363 | 337 |
| Absorption rate: | | | | | were silylated with BSTFA*:TMCS**, in a ratio of 2:1, and the products were analysed using a gas chromatograph which was equipped with a non-polar capillary column and a flame ionization detector. Trimethylolethane was used as the internal standard.

* BSTFA=bis(trimethylsilyl)trifluoroacetamide ≠** TMCS=trimethylchlorosilane

The results are presented in Table 12.

TABLE 12

Emission of polyol from the setting oven

| | | Separate addition of crosslinking agent (citric acid) and polyol | | | Addition of crosslinking agent in the form of a mainly polymerized reaction product which has been prepared in advance | | | | Emission of polyol | |
|---|---|---|---|---|---|---|---|---|---|---|
| | | (glycerol/TMP) | | | Added | | | Added | In exhaust air | |
| | | Citric | | | reaction | Citric | | catalyst | | |
| Sample | Crosslinking agent | acid g/kg* | glycerol g/kg* | TMP g/kg* | product g/kg* | acid mol % | Glycerol mol % | TMP mol % | Na₂HPO₄ g/kg* | Glycerol mg/m³ | TMP mg/m³ |
| A | Citric acid | 35 | 25 | | | | | | | 18.5 | |
| B | CG polymer** | | | | 50 | 50 | 50 | | 10 | 1.3 | |
| C | Citric acid | 38 | | 11 | | | | | 10 | | 6.1 |
| D | Polymer B*** | | | | 60 | 65 | | 35 | 10 | | 0.2 |
| E | Polymer C*** | | | | 60 | 55 | | 45 | 10 | | 0.8 |
| F | Polymer D*** | | | | 60 | 65 | | 35 | 10 | | 0.4 |

*Refers to pulp
**see Experiment 1 and Experimental Series I, Table 9
***see Experiments 6–8 and Experimental Series III TABLE 11-continued

| Crosslinking agent, g/kg | Citric acid 38 TMP 22 | Polymer B)60 | Polymer C)60 | Polymer D)60 |
|---|---|---|---|---|
| 4 × 50 ml | | | | |
| Dosage, 1 ml/s | 1.3 | 1.4 | 1.4 | 1.6 |
| Dosage, 2 ml/s | 1.0 | 0.83 | 1.1 | 1.2 |
| Dosage, 3 ml/s | 0.70 | 0.62 | 0.78 | 0.84 |
| Dosage, 4 ml/s | 0.50 | 0.45 | 0.52 | 0.58 |

Emission of polyol from the setting oven was studied during the crosslinking of fluff pulps with different crosslinking agents, namely when producing the crosslinked, absorbent cellulose pulps which were studied in experimental series I and III. As described above, the setting reactions, i.e. the crosslinking of the dry pulp, were performed at 180° C. for 6 min; heating-up time, 2–4 min. The total quantity of pulp in each test was 165 g. During the whole of the hot period, 1 l/min was removed from the total airflow of 700 l/min for analysing polyol content. This analysis was carried out by gas chromatography, using the so-called GC technique. In this case, a constituent stream of the exhaust air (1 l/min) is conducted to a cooled absorption bottle containing ethanol. NaCl+ice was used as the cooling medium, −14° C. The air samples were taken during the whole of the time for the heating-up and the crosslinking reaction. The sampling those was also rinsed internally with ethanol, since polyols condense in the sampling hose.

The absorption liquid+the hose-rinsing liquid were evaporated in a rotary evaporator. After that, the analytes

TABLE 13

| Sample Table 12 | Polymer | Extractable* citric acid mg/g of pulp | Glycerol* mg/g of pulp | TMP* mg/g of pulp |
|---|---|---|---|---|
| 1 | Citric acid | 15 | 11.3 | |
| 2 | CG polymer | 0.5 | 2.3 | |
| 3 | Citric acid | 0.85 | | 6.7 |
| 4 | Polymer B | 0.19 | | 0.3 |
| 5 | Polymer C | 0.37 | | 1.5 |

*3 g of pulp were shaken with 90 ml of water at room temperature for 1 h. Acid in the extract was analysed by HPLC (high performance liquid chromatography) and polyols by GC.

Samples A and B in Table 12 were analysed for water-extractable material. Fresh samples were prepared like the original samples C, D and E. These samples were likewise analysed for extractable material. The results are summarized in Table 13 above. From the table, it can be seen that the pulp samples which were produced using polymerized crosslinking agent contain smaller quantities of extractable material than the samples produced by adding acid and polyol.

Results Achieved

In summary, use, as crosslinking reagent, of a reaction product which was prepared in advance by reacting a first di-, tri- or poly-functional compound with a polyol resulted in an absorbent cellulose material having, in all essentials, the same desirable product properties as a corresponding cellulose pulp which was crosslinked with corresponding starting chemicals which were not caused to react with each other in advance, but only in conjunction with the setting reaction. However, when using the previously reacted, mainly polymeric/oligomeric crosslinking reagent, a significant decrease in the emission of polyol was achieved when carrying out the setting. By means of the appropriate choice of starting chemicals for preparing the reaction products, it is possible to lower the emission of polyol to a harmless level. The lowest emission levels have so far been achieved using a polymeric reaction product which is prepared by reacting citric acid with TMP. The decreased emission of polyol from the reaction chamber can have the beneficial result of decreasing, or completely eliminating, the need to clean the exhaust air leaving the process equipment.

The fact that the quantity of acid and polyol which can be extracted with water from the manufactured product is decreased also means that the quantity of free chemicals which are present, and which may possibly have an irritating effect on skin, is reduced. This is regarded as being desirable irrespective of the fact that the chemicals employed are regarded as being of relatively low toxicity.

What is claimed is:

1. Method for preparing an absorbent cellulose product having improved compressibility and decreased emissions during production of the product, which method comprises the steps of:
    defibering the cellulose fibers;
    impregnating the cellulose fibers with a quantity, which is effective for crosslinking, of one or more water-soluble polymers which are produced in advance, which have an average molecular weight, Mw, of between 350 and 70,000 g/mol, and which possess free acid or aldehyde groups; wherein said water-soluble polymers have been produced by reacting a first di-, tri- or poly-functional compound with one or more di-, tri- or poly-functional alcohols and wherein said product has a density of at least 230 kg/m$^3$ following application of a pressure of at most 50 bar;
    drying the impregnated substance;
    defibering the impregnated substance at the latest after drying; and
    crosslinking the defibered cellulose fibers, in the dry state, by heating the impregnated, dried and defibered cellulose product.

2. Method according to claim 1, wherein the cellulose product is fluff pulp.

3. Method according to claim 1, wherein the polymers have an average molecular weight of between 350 and 25,000 g/mol.

4. Method according to claim 1, wherein the polymers have an average molecular weight of between 450 and 10,000 g/mol.

5. Method according to claim 1, wherein the defibered cellulose products are crosslinked at a temperature of between 100 and 210° C.

6. Method according to claim 1, wherein the defibered cellulose products are crosslinked at a temperature of between 120 and 200° C.

7. Method according to claim 1, wherein the defibered cellulose products are crosslinked at a temperature of between 140 and 200° C.

8. Method according to claim 1, wherein the fibres are impregnated with an aqueous solution which contains the crosslinking polymer mixture in a quantity within the range from 5 to 100 g of crosslinking reaction product per kg of cellulose fibre.

9. Method according to claim 1, wherein the fibres are impregnated with an aqueous solution which contains the crosslinking polymer mixture in a quantity within the range from 20 to 60 g per kg of cellulose fibre.

10. Method according to claim 1, wherein the defibering is carried out in the dry state at a dry matter content which exceeds 80%.

11. Method according to claim 1, wherein the defibering is carried out in the dry state at a dry matter content which is between 90 and 95%.

12. Method according to claim 1, wherein the defibering is carried out in the wet state at a dry matter content of 30–80%.

13. Method according to claim 1, wherein the defibering is carried out in the wet state at a dry matter content of 40–55%.

14. Method according to claim 1, wherein the crosslinking reaction is carried out with a dwell time of between 1 and 20 minutes.

15. Method according to claim 1, wherein the crosslinking reaction is carried out with a dwell time of between 4 and 10 minutes.

16. Absorbent cellulose product having improved compressibility and decreased emissions during production of the product, said product, comprising cellulose fibers which are crosslinked in the dry, defibered state by reaction with an effective quantity of one or more water-soluble polymers which are prepared in advance, which have an average molecular weight of between 350 and 70,000 g/mol, and which possess free acid or aldehyde groups, wherein said polymers have been produced by reacting a first di-, tri- or poly-functional compound with one or more di-, tri- or poly-functional alcohols; wherein said product is has a density of at least 230 kg/m$^3$ following application of a pressure of at most 50 bar, wherein said product is crosslinked by reacting the cellulose fibers, in the dry state, with said effective quantity of said one or more polymers which have been prepared in advance; wherein the crosslinking substance consists of a mixture of a number of polymers, which mixture includes reaction products selected from the group consisting of FP, FP$_2$, F$_2$P and F$_2$P$_2$ type, where F is derived from said first compound, which contains functional groups of the types of groups which include acid anhydride or di-, tri- or poly-functional carboxyl groups or aldehyde groups, and P is derived from a polyfunctional alcohol.

17. Absorbent cellulose product having improved compressibility and decreased emissions during production of the product, said product comprising cellulose fibers which are crosslinked in the dry, defibered state by reaction with an effective quantity of one or more water-soluble polymers which are prepared in advance, which have an average molecular weight of between 350 and 70,000 g/mol, and which possess free acid or aldehyde groups, wherein said water-soluble polymers have been produced by reacting a first di-, tri- or poly-functional compound with one or more di-, tri- or poly-functional alcohols and wherein said product has a density of at least 230 kg/m$^3$ following application of a pressure of at most 50 bar.

18. Absorbent cellulose product according to claim 17, wherein the polymers have an average molecular weight of between 350 and 25,000 g/mol.

19. Absorbent cellulose product according to claim 17, wherein the polymers have an average molecular weight of between 450 and 10,000 g/mol.

20. Absorbent cellulose product according to claim 17, wherein said polymers possess carboxyl groups or aldehyde groups.

21. Absorbent cellulose product according to claim 17, wherein the crosslinking substance consists of a mixture of a number of polymers, which mixture includes reaction products selected from the group consisting of the FP, $FP_2$, $F_2P$ and $F_2P_2$ type, wherein F is derived from said first compound, which contains functional groups of the types of groups which include acid anhydride or di-, tri- or poly-functional carboxyl groups or aldehyde groups, and P is derived from a polyfunctional alcohol.

22. Absorbent cellulose product having improved compressibility and decreased emissions during production of the product, comprising cellulose fibers which are crosslinked in the dry, defibered state by reaction with an effective quantity of one or more water-soluble polymers which are prepared in advance, said polymers having an average molecular weight of between 350 and 70,000 g/mol, and possessing free acid or aldehyde groups, wherein said water-soluble polymers have been produced by reacting a first di-, tri- or poly-functional compound with one or more di-, tri- or poly-functional alcohols and wherein said product has a density of at least 230 kg/m$^3$ following application of a pressure of at most 50 bar.

* * * * *